(12) United States Patent
Harris

(10) Patent No.: US 7,330,305 B2
(45) Date of Patent: Feb. 12, 2008

(54) LASER SCANNING CONFOCAL MICROSCOPE WITH FIBRE BUNDLE RETURN

(75) Inventor: Martin Harris, Windsor (AU)

(73) Assignee: Optiscan Pty Ltd, Notting Hill (AU)

(*) Notice: Subject to any disclaimer, the term of this patent is extended or adjusted under 35 U.S.C. 154(b) by 266 days.

(21) Appl. No.: 10/510,175

(22) PCT Filed: Apr. 24, 2003

(86) PCT No.: PCT/AU03/00491

§ 371 (c)(1),
(2), (4) Date: Oct. 4, 2004

(87) PCT Pub. No.: WO03/090613

PCT Pub. Date: Nov. 6, 2003

(65) Prior Publication Data

US 2005/0174425 A1    Aug. 11, 2005

(30) Foreign Application Priority Data

Apr. 26, 2002 (AU) .......................... PS2000
May 24, 2002 (AU) .......................... PS2556

(51) Int. Cl.
*G02B 21/00* (2006.01)
(52) U.S. Cl. .............. 359/368; 359/634; 385/117; 356/303
(58) Field of Classification Search .............. None
See application file for complete search history.

(56) References Cited

U.S. PATENT DOCUMENTS

| 5,659,642 A | 8/1997 | King et al. |
| 6,038,067 A * | 3/2000 | George .................... 359/368 |
| 6,337,842 B1 | 1/2002 | Wolfer et al. |
| 6,377,842 B1 | 4/2002 | Pogue et al. |
| 6,456,769 B1 * | 9/2002 | Furusawa et al. ........ 385/117 |
| 6,747,795 B2 | 6/2004 | Lin et al. |

FOREIGN PATENT DOCUMENTS

JP        11133306        5/1999

OTHER PUBLICATIONS

Gmitro, "Confocal microscopy through a fibert-optic imaging bundle", Apr. 15, 1993, vol. 18, No. 8, Optics Letters, pp. 565-567.

* cited by examiner

*Primary Examiner*—Stephone B. Allen
*Assistant Examiner*—Derek S. Chapel
(74) *Attorney, Agent, or Firm*—Stites & Harbison PLLC; Douglas E. Jackson

(57) ABSTRACT

The invention provides a confocal microscope or endoscope, having a source of coherent light for illuminating a sample, and an imaging optical fibre bundle (82) for receiving return light, whereby the fibre bundle (82) provides a return channel for fluorescent return light (78). The optical fibre bundle (82) preferably preserves, between entry and exit ends of the bundle, the relative spatial coordinates of the cores of individual fibres constituting the bundle.

21 Claims, 15 Drawing Sheets

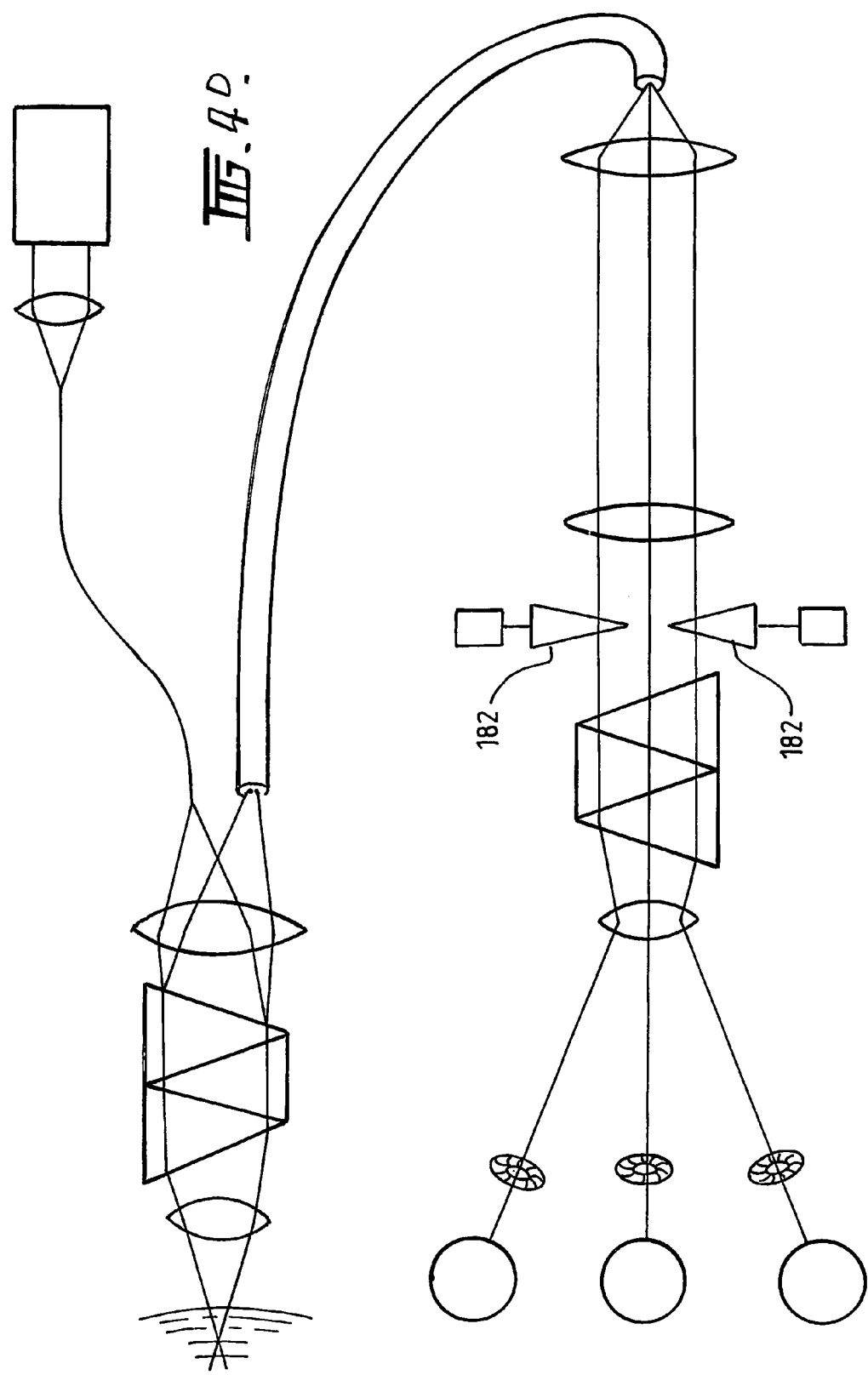

LASER SCANNING CONFOCAL MICROSCOPE WITH FIBRE BUNDLE RETURN

FIELD OF THE INVENTION

The present invention relates to a laser scanning confocal microscope with fibre bundle return, for, in particular, improving the optical performance of laser scanning confocal microscopes. The invention may also have application in the miniaturisation of confocal endomicroscopes, in devices such as well plate readers, DNA chip scanners, in remote spectroscopy and as an optical system for a laser scanning ophthalmoscope.

BACKGROUND OF THE INVENTION

Existing two fibre confocal microscopes and endoscopes typically require precise fibre positioning and alignment in the probe head to provide separation of the light path. Existing systems also commonly require an extended beam path or further beam compressor optics in the microscope or endoscope head to give variable pinhole capability.

SUMMARY OF THE INVENTION

The present invention provides a confocal microscope or endoscope, having:
  a source of coherent light for illumination of a sample;
  a light focusser for receiving and focussing said coherent light to an illumination volume that in use intersects said sample;
  a beam-splitter for receiving return light returned from said sample in response to said illumination and for diverging from said return light a fluorescent component of said return light; and
  an imaging optical fibre bundle comprising a plurality of individual fibres, having an entry end located to receive said diverged fluorescent component of said return light so that said diverged fluorescent component is transmitted to an exit end of said fibre bundle;
  wherein said fibre bundle preserves, between said entry end and said exit end of said fibre bundle, the relative spatial coordinates of the cores of said individual fibres.

Thus, a return channel is provided that can be made optically independent and isolated from the laser delivery fibre fluorescence (and therefore decrease optical noise). The optical fibre bundle, being intended for imaging purposes, preserves, in a comparison of the entry and exit ends of the bundle, the relative spatial coordinates of the cores of the individual fibres. Within this constraint, however, it is acceptable to transform these coordinates between the ends provided an image can still be formed. Thus, for example, the coordinates could be reversed so that a mirror image is formed. Other transformations, as will be apparent to those skilled in this art, are also possible. This constraint (i.e. that an image can be formed) means that the bundle might be termed 'coherent' in the sense that the fibre bundle maintains image orientation; this should not be confused with the coherence of the light from the light source, which refers to the maintenance of light propagation properties within the illuminating fibre.

Further, this condition that the fibre bundle maintains image orientation only relates to the two ends of the fibre bundle. Thus, while a fused fibre bundle may be employed in some applications, in other applications the fibres may not be fused between the ends of the bundle, as long as the ends preserve a sufficient 'coherence' (i.e. image orientation maintenance) for the bundle to function as an imaging bundle. This latter type of bundle also has the advantage of greater flexibility over its length.

It will also be understood that the term "confocal" is employed—as is understood in the art—to include conjugate focal point geometries that may not be purely confocal owing to the finite size of apertures, spatial filters, etc., and the occasional desirability of increasing the amount of detected light even if this means a minor loss of resolution. Such arrangements are nevertheless referred to as confocal (and are embraced by that term herein), as the collected light includes what might be termed 'pure' confocal return light.

Preferably the microscope or endoscope further comprises a single mode fibre for transmitting said coherent light from said source and having an exit end mounted in a fixed spatial relationship to said entry end of said fibre bundle.

The microscope or endoscope may be embodied as an ophthalmoscope, colonoscope or other optical instrument.

Preferably the beam-splitter comprises a simple or compound prism. Alternatively, the beam-splitter could comprise a transmission or reflection diffraction grating.

Preferably said microscope or endoscope includes a further beam-splitter, optically reversed relative to said beam-splitter and located optically after said fibre bundle, to improve focal plane isolation.

Thus, in one embodiment, said beam-splitter comprises a simple or compound prism, and said microscope or endoscope includes a further prism, optically reversed relative to said prism and located optically after said fibre bundle, to improve focal plane isolation.

Preferably said microscope or endoscope includes a spatial filter optically after said fibre bundle. More preferably said spatial filter comprises a variable aperture (such as a pinhole).

Preferably said microscope or endoscope includes a scanner for providing scanning of said illumination volume relative to said sample.

In one embodiment said scanner comprises a mirror, in another said scanner comprises a tuning fork. In one embodiment, said scanner comprises a pivotably mounted member provided with collimating optics for collimating said coherent light.

Preferably said collimating optics comprises a simple or compound lens.

Preferably said pivotably mounted member is mounted by means of, and is pivotable about, an axle. Alternatively, said pivotably mounted member is mounted by means of a pair of flexible supports that differ (preferably in length) so that said pivotably mounted member can be pivotted by being oscillated.

Preferably said microscope or endoscope includes one or more shallow angle prisms located in an image plane to separate out different spectral bands, and a plurality of fibre bundles, each for receiving a respective spectral band, for producing multiple colour images. Preferably said microscope or endoscope includes a plurality of separate photodetectors, each for detecting a respective spectral band transmitted by a respective fibre bundle.

BRIEF DESCRIPTION OF THE FIGURES

In order that the invention may be more clearly ascertained, embodiments will now be described, by way of example, with reference to the accompanying drawings, in which:

FIG. 4D is a simplified view of a modification of the embodiment of FIG. 4A, in which shallow angle prisms are located in the image plane to separate out different spectral bands and direct them to separate photo-detectors to produce multiple colour images;

DETAILED DESCRIPTION

Figure 1:
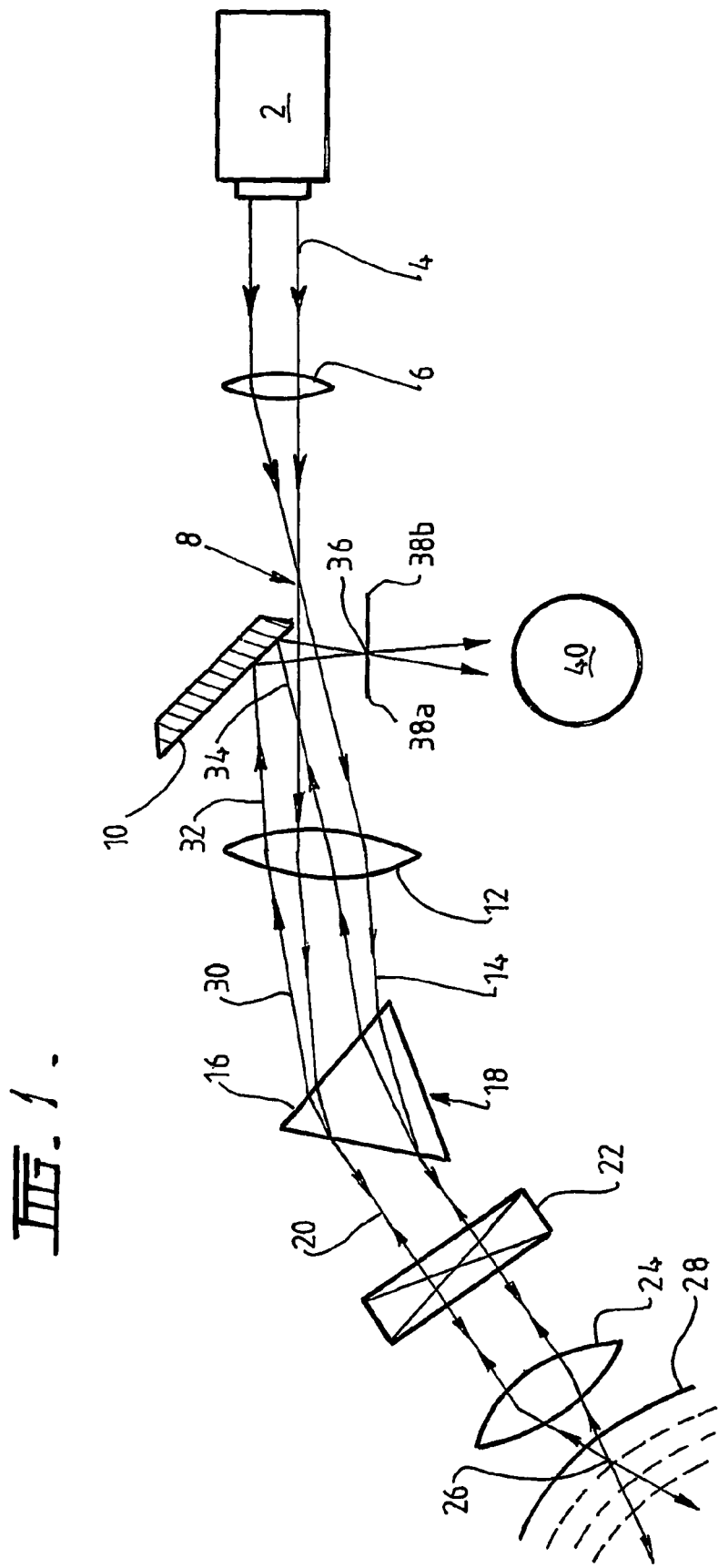
FIG. 1 is a schematic view of an optical arrangement in which a prism is used as a beam-splitter (though not embodying the present invention)

FIG. 1 illustrates how a prism can be used as a beam-splitter in an optical system suitable for a laser scanning confocal microscope in fluorescent imaging mode, though without—in this figure—embodying the present invention. A laser source 2 provides a laser beam 4, which is focussed by a lens 6 to a Gaussian waist 8 adjacent to the edge of a plane mirror 10. The light then diverges from this focus 8 until it meets a collimating lens 12, which collimates the beam 14 and projects it onto the face 16 of a glass prism 18.

The laser beam is TEMoo and monochromatic, and hence emerges from the prism 18 as a beam 20 with an unchanged parallel set of wave fronts. The beam passes through an XY scanner 22 and is focussed by a focussing lens 24 as diffraction limited spot 26 within the tissue sample 28. Fluorescence generated by the laser light in the tissue is Stokes shifted to longer wavelength than the wavelength of the excitation light from the laser. Fluorescent light from the focussed spot region returning through the focussing lens 24 retraces the same general set of ray paths 20 through the XY scanner 22 until it reaches the prism 18.

Longer wavelengths are less refrangible in a normal dispersion regime than is laser light, so the longer wavelengths of the return light emerge from the prism 18 as a beam 30 at an angle with respect to the incoming laser beam 14. The beam 30 is converged by collimating lens 12 and the rays indicated by 32 and 34 are reflected by the mirror 10 to a focus 36. Combined with fluorescence of longer wavelengths, the light is deflected by mirror 10 and focuses to form a linear spectrum 38a to 38b. All these beams of the full range of fluorescent wavelengths pass to a photomultiplier tube 40, which generates an electrical signal.

A pair of knife edges (not shown) is located at the focus just above and just below the plane of the figure at the focus 36. These define a slit through which the spectral line passes. Light from out of focus planes will largely be blocked by the jaws of the slit allowing for the isolation of the focal plane. The width of the split can be adjusted to control the degree of focal plane isolation.

The optical configuration shown in FIG. 1, however, does not offer very much of an advantage in the miniaturisation process. The slit mechanism, and the photomultiplier tube are large and both need to be located in the head to implement this design.

Prism Beam-Splitter with Fibre Return

A major advantage is obtained by transferring the image of the slit plane out of the head and into the detector unit. This could be done using a flexible optic transfer element of small cross sectional area. A suitable component for doing this would be a "coherent" (i.e. an image orientation maintaining fibre bundle) optic fibre bundle or imaging bundle.

Figure 2:
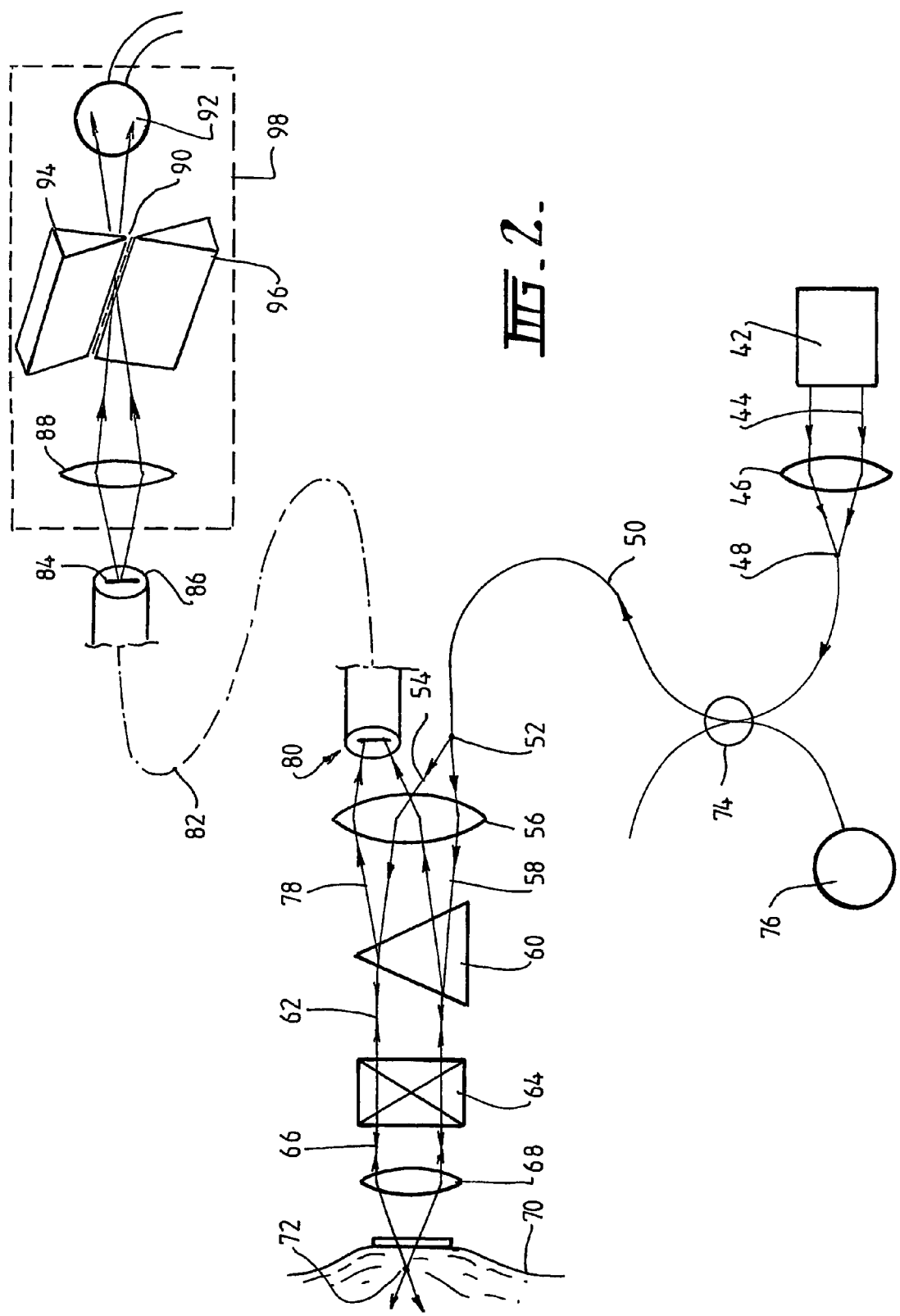
FIG. 2 is a schematic view of a laser scanning confocal microscope with fibre bundle return according to one embodiment of the present invention.

FIG. 2 is a schematic view of a laser scanning confocal microscope with fibre bundle return according to one embodiment of the present invention, using a simple equilateral prism as a beam-splitter and a "coherent" (i.e. image orientation maintaining) optic fibre bundle. The Stokes shifted fluorescence returning from the focussed laser spot is moved by the prism laterally to fall as a line on the polished tip of a fibre bundle. This fibre bundle carries the fluorescent light back to the detector unit. This arrangement would facilitate factory adjustment and on site alignments would be considerably easier.

The fluorescence, being broadband, is spread out over a large number of return fibres, which eliminates the need for XY positioning of the optical return transfer element in the head to enable the line to impinge on the photomultiplier tube. It may be seen from FIG. 2 that any final adjustment of the system could be carried out in the detector unit. It is also clear that slit positioning precision and adjustment tolerances in the detector unit can be relaxed because the light selection is being carried out on a highly magnified image of the bundle tip in the detector unit.

In FIG. 2 a laser 42 provides a beam of TEMoo light 44, which is focussed by focussing lens 46 to the tip 48 of a single mode optic fibre 50. The light travels along the fibre core and emerges from the fibre tip 52 as a divergent beam 54. The light is collimated by collimating lens 56 to form a beam 58 that passes though a glass prism 60 from which it emerges as beam 62. Passing through the prism does not change the beam, as the light is monochromatic. The beam 62 is then deflected as an acquisition raster by the XY scanner 64. The scanned beam 66 is then focussed by focussing lens 68 through tissue sample 70 to a focussed spot 72. The reflected and fluorescent light from this spot retraces the same general set of ray paths back through focussing lens 68, is descanned by the XY scanner 64 and travels along beam path 62 to prism 60.

Light that has been reflected or scattered from the focal spot 72 (being of unchanged wavelength) travels back along ray path 58 through collimating lens 56 and focuses back into the optic fibre 50. This light is split off by a fused biconical taper coupler 74 to a photomultiplier tube 76 to allow the formation of a reflection image. Light generated by fluorescence at the focal volume also retraces the same general set of ray paths as the reflected light until it reaches the prism. Fluorescence is always of a longer wavelength than the excitation wavelength. Hence the fluorescent light is deflected by a smaller angle on passing through the prism 60 than the reflected excitation light and forms a beam 78.

The beam 78 passes through collimating lens 56 and is focussed onto the polished end 80 of a 'coherent' (i.e. an image orientation maintaining) fibre optic bundle 82. The fluorescence is broad banded, that is, it consists of a range of wavelengths. Hence it is actually focussed as a spectral line on the end 80 of the bundle 82, which is transmitted by the 'coherent' array of fibres constituting the bundle 82 to an image 84 on the exit end 86 of the bundle 82. A lens 88 projects a magnified image 90 in space of the line 84 and the fibre bundle 82. The light forming this image 90 continues on to impinge on the photomultiplier tube 92 and generates an electrical signal, which forms the image. A pair of adjustable jaws 94 and 96 are provided which form a slit in width to allow a selected fraction of the near confocal fluorescent light to pass to the photomultiplier tube 92, so that the depth of field isolation can be controlled.

The last stages of the optics (carrying the light from fibre tip 86 to the photomultiplier tube 92) are enclosed in a light tight box 98, thereby forming a module comprising the light tight box 98 and its contents. This enclosed module of the system is referred to below as the Detector Unit.

Figure 3A:
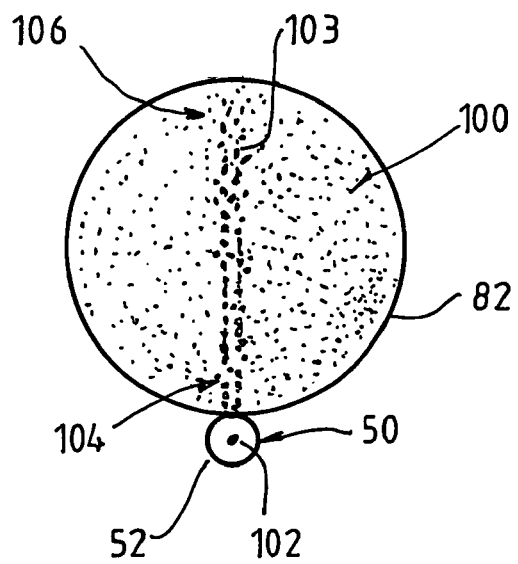
FIG. 3A is a schematic view of the exit end of the beam delivery fibre and entry end of the fibre bundle of the confocal microscope of FIG. 2.
Figure 3B:
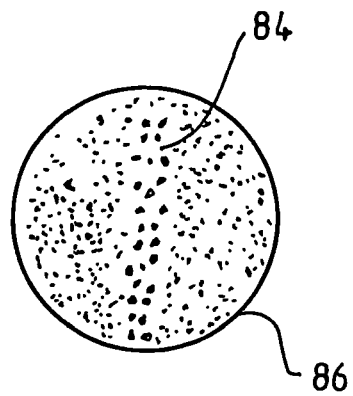
FIG. 3B is a schematic view of the exit end of the fibre bundle of the confocal microscope of FIG. 2.
Figure 3C:
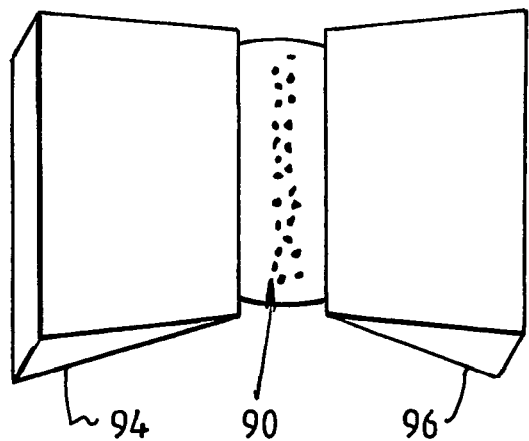
FIG. 3C is a schematic view of the exit end of the beam delivery fibre imaged between the jaws of the slit of the confocal microscope of FIG. 2.

FIG. 3A shows a view of the tip 52 of the laser delivery fibre 50 and the tips 100 of the fibre bundle 82 in the microscope head. The laser delivery fibre 50 has a core 102. The fibre bundle 82 has cores packed together each one of which can accept fluorescent light returning from the specimen. The confocal fluorescent return light forms a line 103 on the bundle end. If blue excitation light is used, the green end of the fluorescent spectrum will fall at 104 while the red end of the fluorescent spectrum will fall at 106. FIG. 3B shows the exit end 86 of the bundle 82, with the light emerging from the spectral line 84. FIG. 3C shows the projected image of the fibre bundle 82 with the spectral line 90 between the two jaws 94 and 96 of an adjustable slit.

Figure 3D:
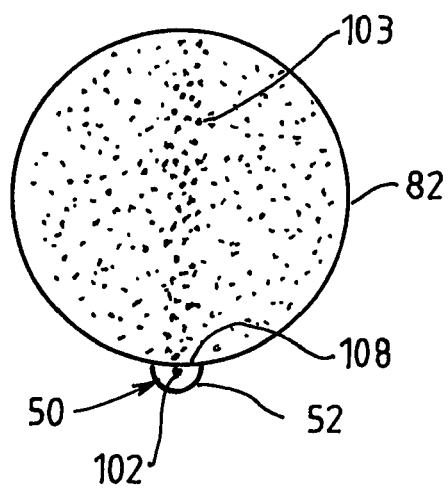
FIG. 3D is a schematic view of a variation of the arrangement shown in FIG. 3A.

FIG. 3D depicts a variation of the arrangement of FIG. 3A, and shows the end of the fibres in the microscope head. The confocal collection fibres 100 of the bundle 82 again collect light along the spectral line 103. However, in this variation the delivery fibre 50 has one side 108 ground flat towards the core 102. This brings the point from which light is emitted (i.e. the core 102) closer to the cores of the fibre bundle 82, which minimizes "spot wander" (defined below)

with fibre tip scanning. It also allows imaging to be carried out using fluorescence, which is closer in wavelength to the excitation wavelength. In this embodiment, the shape of the bundle could also be altered so that the core 102 of fibre 50 is still closer—or even within—the bundle 82, reducing or eliminating the amount of divergence that is required to be provided by prism 60.

A weakness of this first embodiment is that the isolation of the focal plane is not as great as the confocal isolation obtained with fibre or bulk optics pinholes. It would in fact be quantitatively the same as that of a slit scanning confocal system (inverse d) rather than the higher degree of confocal isolation obtained with a pinhole confocal return (inverse $d^2$).

Figure 4A:
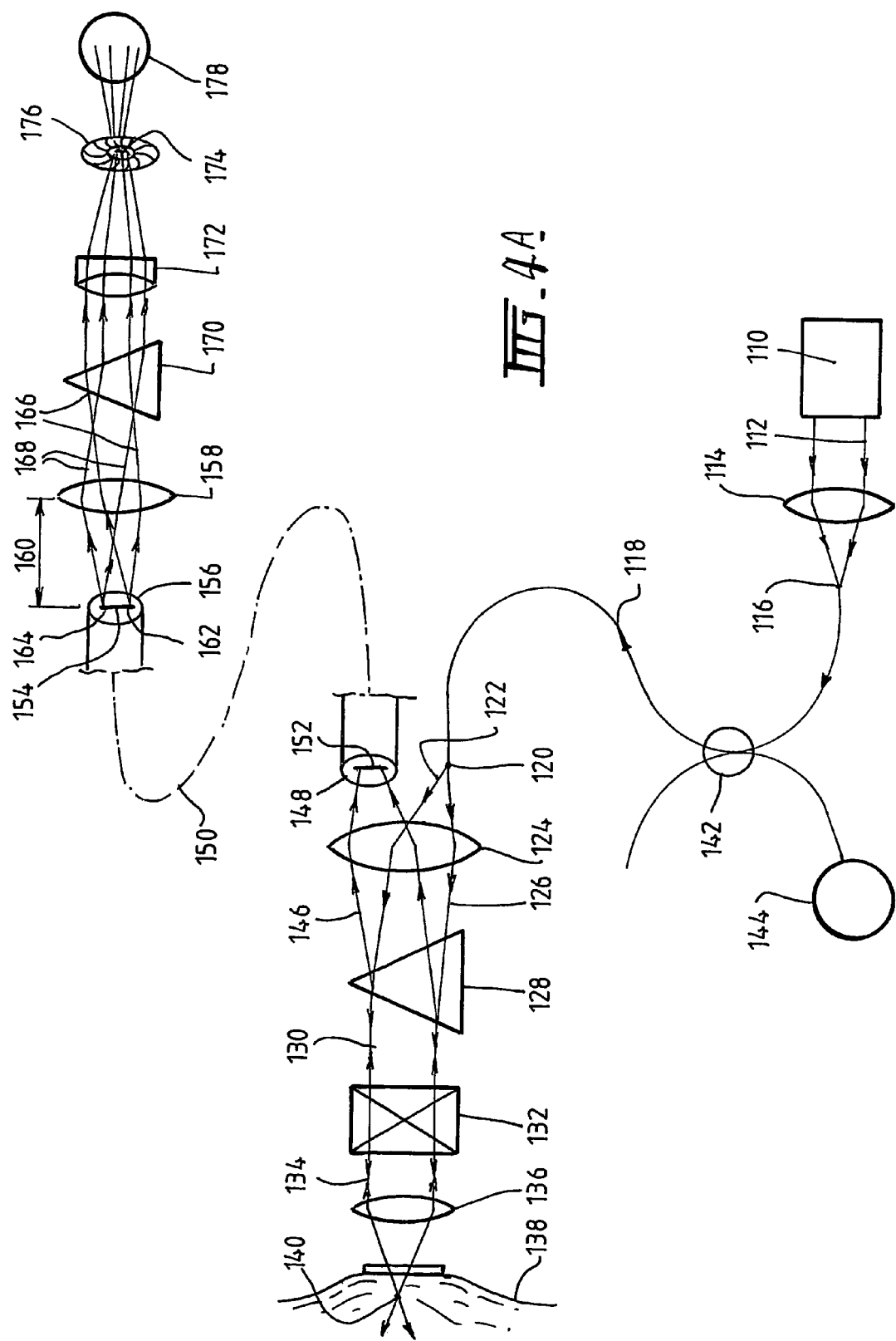
FIG. 4A is a schematic view of a laser scanning confocal microscope with fibre bundle return according to a further embodiment of the present invention.

This can be addressed as shown in the embodiment of FIG. 4A by means of a second (identical) prism placed in the beam path in the Detector Unit. Referring to FIG. 4A, the second prism is orientated so that its effect is in opposition to the effect of the prism (cf. prism 60 in FIG. 2) in the microscope head. The principle of reciprocity in optical ray diagrams will result in the light from the focussed spectral line on the fibre bundle tip being re-focussed to a spot which passes through a variable iris diaphragm placed in front of the photomultiplier tube. Light from the out of focus fluorescence incident on the fibre bundle and returning to the detector unit will be focussed by the detector unit lens and prism as a spot surrounded by near confocal return light. This will have a radially symmetrical light distribution, which is close to spatially identical with a normal confocal pinhole return.

Thus, in FIG. 4A laser 110 provides a beam of TEMoo light 112, which is focussed by focussing lens 114 to the tip 116 of a single mode optic fibre 118. The light travels along the fibre core and emerges from exit end 120 of fibre 118 as a divergent beam 122. It is collimated by collimating lens 124 to form a beam 126 that traverses through a glass prism 128 as a beam 130. As mentioned above, passing through the prism does not change the beam as the light is monochromatic. The beam 130 is then deflected as an acquisition raster by the XY scanner 132. The scanned beam 134 is then focussed by focussing lens 136 through tissue sample 138 to a focussed spot 140. The reflected and fluorescent light from this spot retraces the same general set of ray paths back through focussing lens 136 and is descanned by the XY scanner 132 and travels along beam path 130 to prism 128. Light which has been reflected or scattered from the focal spot 140, being of unchanged wavelength, travels back along ray path 126 through collimating lens 124 and is focussed back into the optic fibre 118. This light can be split off by a fused biconical taper coupler 142 to a photomultiplier tube 144 to form a reflection image.

Light generated by fluorescence at the focal volume also retraces the same general set of ray paths as the reflected light until it reaches the prism 128. Fluorescence is always of a longer wavelength than the excitation wavelength, so the fluorescent light is deflected by a smaller angle on passing through the prism than the reflected excitation light and it forms a beam 146. This beam 146 passes through collimating lens 124 and is focussed onto the polished end 148 of a 'coherent' (i.e. image orientation maintaining) fibre optic bundle 150. The fluorescence is broad banded, that is, it consists of a range of wavelengths. Hence it is actually focussed as a spectral line 152 on the end of the bundle. This is transmitted by the 'coherent' array of fibres to form an image of the line 154 at the exit end 156 of the bundle 150. A lens 158 is situated optically after the exit end 156 of the bundle 150, the distance 160 between the exit end 156 and the lens 158 being the focal length of the lens 158. Light from the green end 162 of the spectral line 154 (i.e. green fluorescence from blue light excitation) emerges from the fibre bundle and is collimated as beam 166. Light from the red end 164 of the fluorescence spectral line is also collimated as a beam 168. The green collimated beam and the red collimated beam are at an angle to one another but, when they pass through a second prism 170, the green beam is refracted by a greater angle and both beams end up travelling parallel to one another. Thus when they enter an achromatic lens 172 they all are focussed to a single diffraction limited spot 174, which passes through the central aperture of an iris diaphragm 176 and impinges on a photomultiplier tube 178 to produce the electrical signal.

Figure 4B:
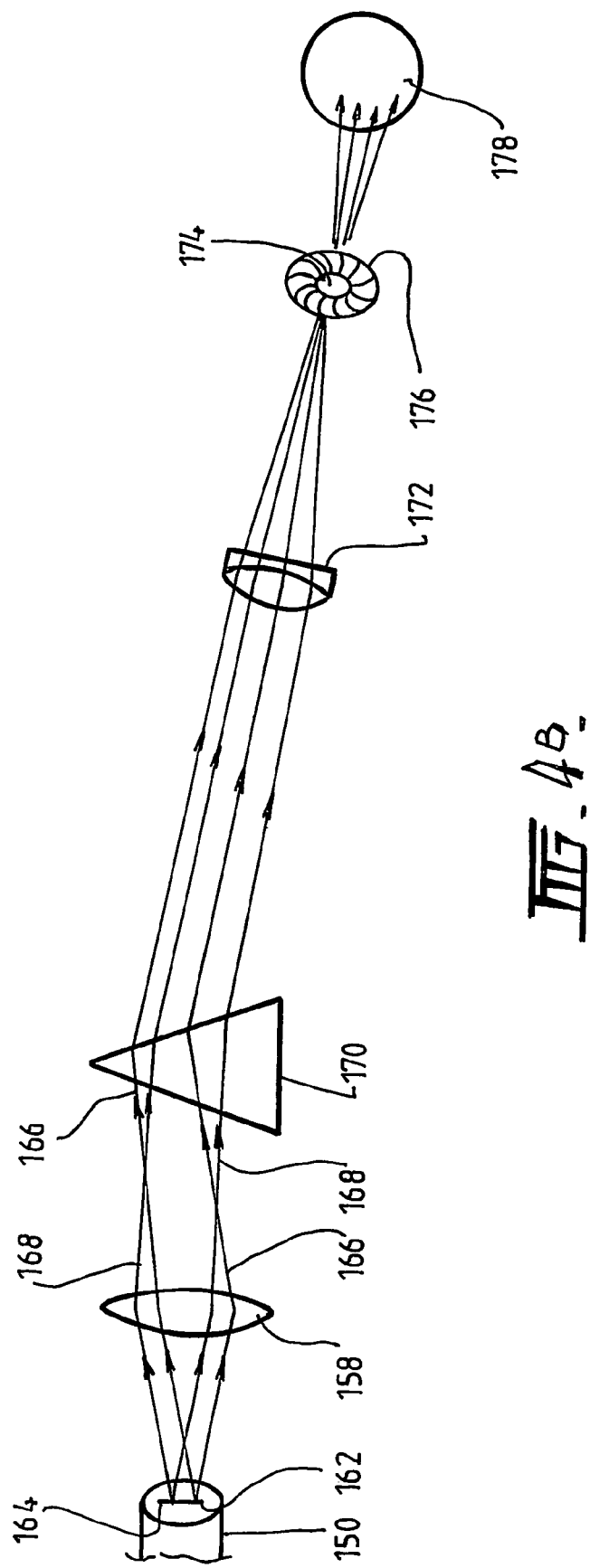
FIG. 4B is an enlargement of the final light path region (i.e. the Detector Unit) of the laser scanning confocal microscope of FIG. 4A.

FIG. 4B is an enlargement of the final light path region (i.e. the Detector Unit) of the system of FIG. 4A. Out of focus return light emitted from other parts of the fibre bundle tip will also undergo deflection by the prism to a degree dependent on its colour. Thus confocal and near confocal return light will be reassigned back to a normally radially symmetrical disposition and thus the operation of the iris diaphragm can be used to vary the depth of field of the imaged plane within the specimen.

Fibre Tip Scanning (Tuning Fork Design)

In previous embodiments the scanning mechanism has been located so as to act after the excitation light has left the prism. This implies that the scanning mechanism would generally be an XY mirror pair or would use a specimen scanning or lens scanning arrangement. It is desirable to be able to use fibre tip scanning mechanisms, such as those in which the exit tip of the fibre is vibrated.

Figure 4C:
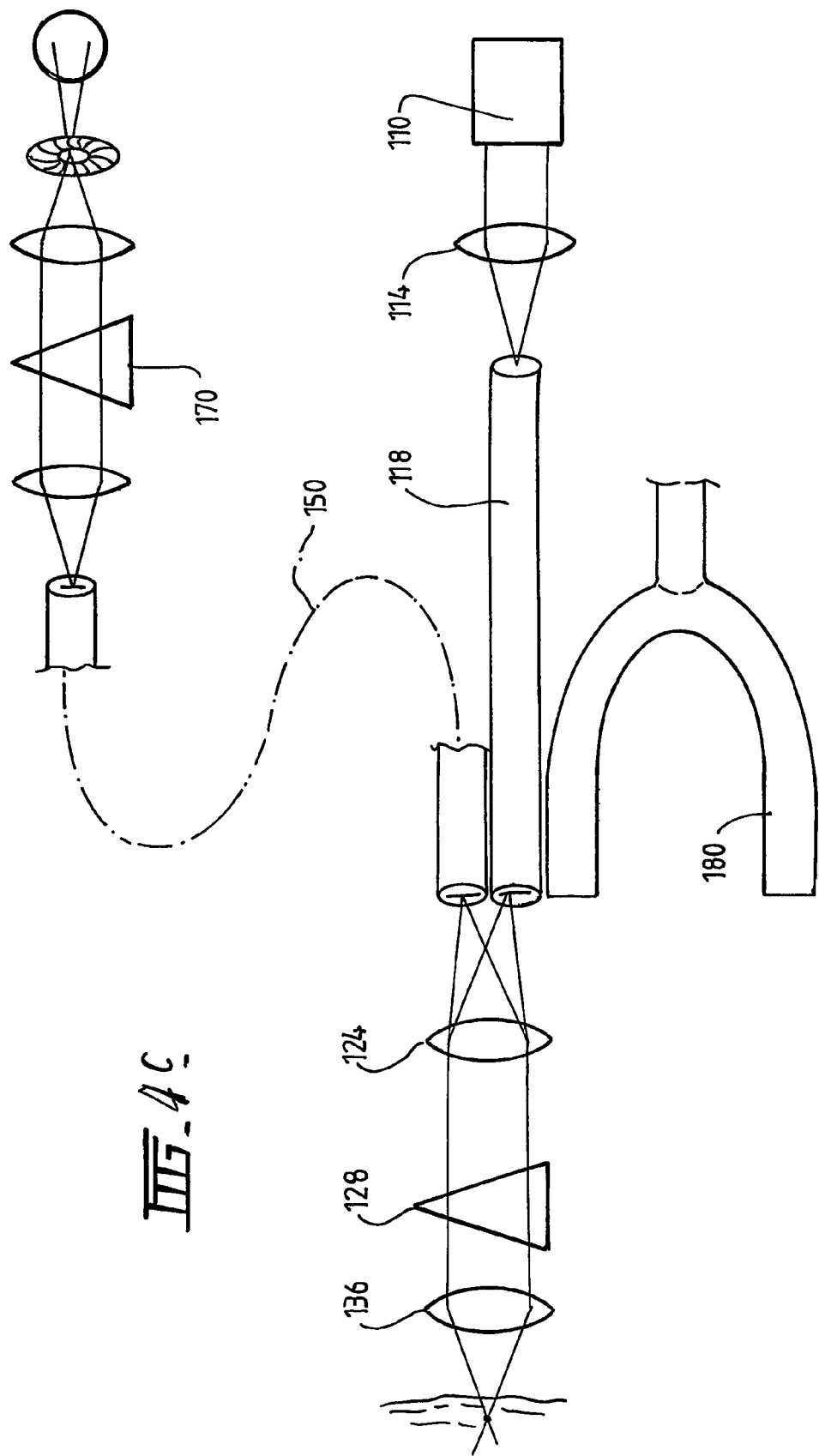
FIG. 4C is a simplified view of a modification of the embodiment of FIG. 4A, in which scanning is performed by means of a tuning fork and the fibre bundle is positioned to be scanned synchronously with the laser delivery fibre.

FIG. 4C shows how it would be possible to position the fibre bundle 150 so that it is scanned synchronously on the same vibrating assembly 180 (comprising a tuning fork) as the laser delivery fibre 118 in front of the collimating lens. This could be done with a tuning fork fast scan motion as shown in the figure, which replaces—in effect—the scanning mirror assembly 132 and permits further miniaturisation.

The prism beam-splitter principle also addresses the problem of finding a way in which the confocal return fibre pinhole can be scanned in exact synchrony with the scan of the laser excitation fibre.

Return 'Spot Wander' resulting from Prisms Aberrations

Fibre tip scanning introduces a difficulty with prism-based beam-splitter systems. Fluorescence of any particular Stokes shift, say 488 nm→520 nm, causes the confocal return spot of the 520 nm light to focus at a position which is displaced laterally from the emitting core of the laser light delivery fibre. For a two-fibre tuning fork system to work successfully it is important that the displacement of the confocal return spot is maintained at a fixed and constant displacement distance from the emitting core at the tuning fork tine. However prism (and polarisation based) compact design beam-splitter systems give varying distance of displacement if the scanning is done before the laser light enters the prism. If uncorrected this would result in a substantial vignetting of the image.

There are two mechanisms responsible for this, one being exhibited for scanning motions of the emitting fibre tip in planes, which are parallel to the plane of symmetry of the prism, the other which is exhibited by scanning in the orthogonal directions.

Fortunately there are a number of ways of minimising or eliminating these problems. Listed below are a number of methods that can do can this, however, it is possible that there may be further ways that could also work just as well.

The first method is to use the fact that both mechanisms produce spot wander in the same direction i.e. in the direction of the spectral line. Hence an optical system in which the slit mechanism was used to isolate the focal plane would eliminate the effects of both aberrations.

The effects can be more easily dealt with by the use of a compound prism designed so that the fluorescence emission wavelengths were all bunched up close together in the spectrum but were well separated in the spectrum from the excitation wavelength.

In general both effects can be minimised (and possibly made insignificant) by designing the scanning optics so that the laser emission fibre tip is brought as close as possible to the tip of the fibre bundle, (still being coplanar with the flat polished tip). This can be achieved by polishing down one side of the cladding of the laser emitting fibre (as in FIG. 3D) or by etching down the cladding using an ammonium bifluoride solution.

The use of an Amici (direct vision spectroscope) prism will eliminate one form of spot wander.

Another way of compensating would be to carry out synchronous mechanical scanning of the light beam via optical components in the Detector Unit. This, however, may introduce extra mechanical complexity in some embodiments.

A number of other optical configurations specified under the systems heading "Hybrid Systems" would also reduce or eliminate these aberrations.

Systems in which the scan mechanisms operate between the prism and the specimen or patient can be employed to reduce or eliminate these aberrations.

Optical Design Producing Spectral Separation of Two or More Channels of Fluorescence The prism in the head produces spectral separation, which is maintained in the fibre bundle and projected as a real image of the spectrum (and the transfer fibres) in the Detector Unit. This spectral separation is desirable for dual channel (stain/counterstain) labelling. Mirrors or shallow angle prisms can be located in this image plane to separate out different spectral bands and direct them to separate photo-detectors to produce two or three colour images or even more channels if desired. A convenient way to achieve this using shallow angle prisms 182 is shown in FIG. 4D; this embodiment is shown with direct vision prisms but this is not essential for the operation of the device. This embodiment is more compact and has some other advantages over a sliding mirror system.

Scanning in Remote Fluorescence Spectroscopy and Gene Chip Readers

Figure 4E:
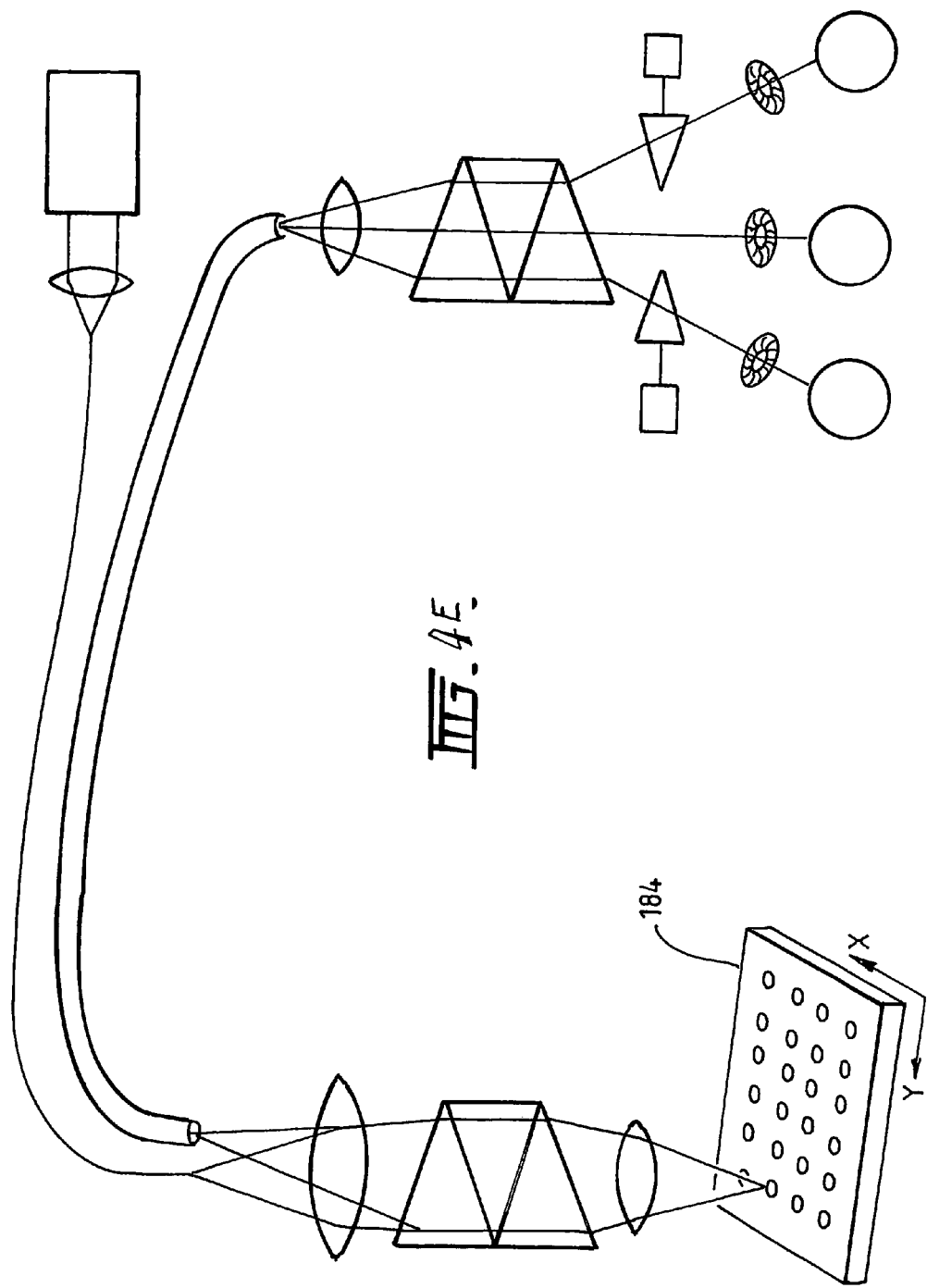
FIG. 4E is a simplified view of a modification of the embodiment of FIG. 4A, in which the sample is in the form of a translatable gene chip.
Figure 4F:
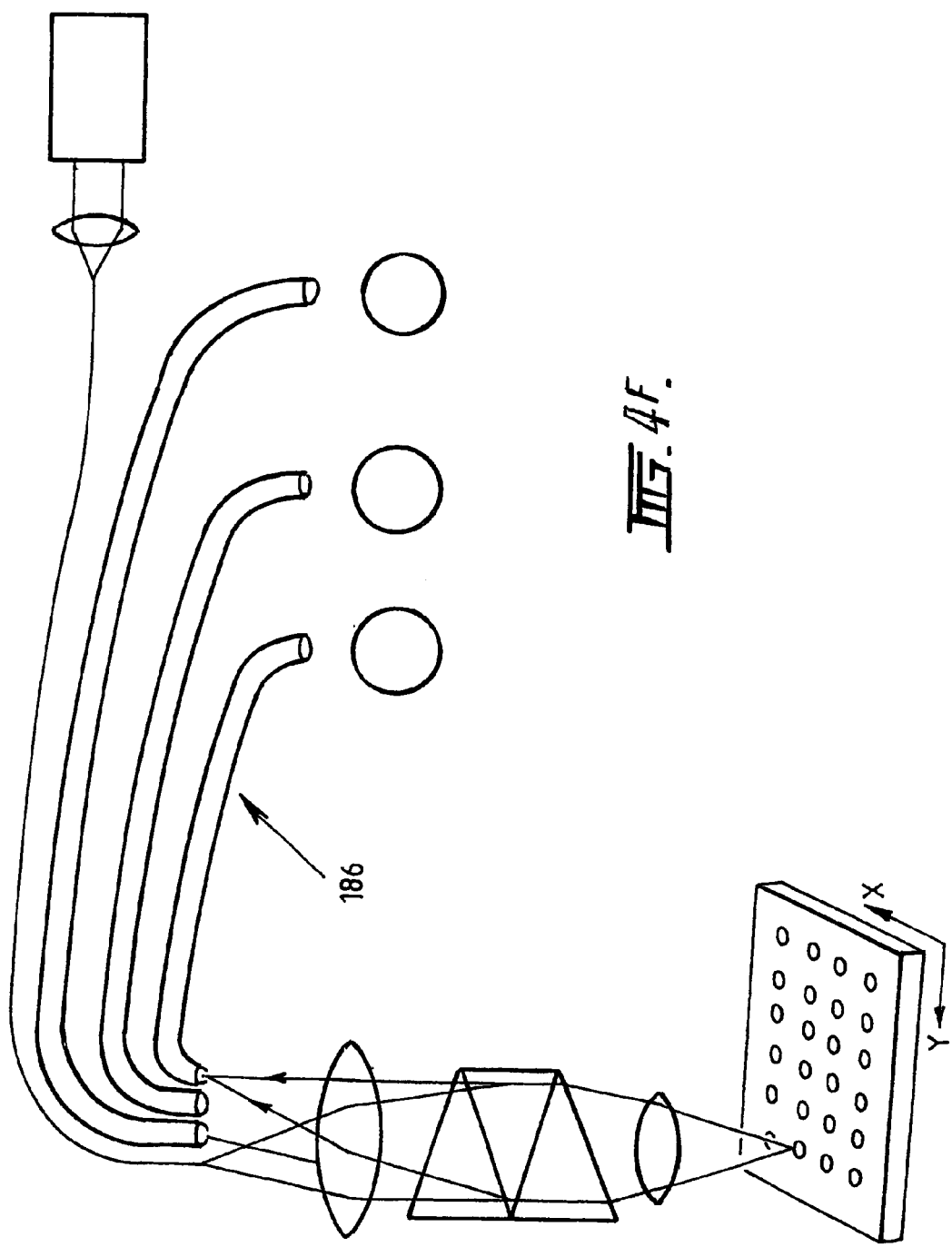
FIG. 4F is a simplified view of a modification of the embodiment of FIG. 4A, in which the sample is in the form of a translatable gene chip and the microscope includes a line of fibre bundles.

For applications in remote spectroscopy, plate readers or gene chip readers these considerations of prism aberration correction methods are probably immaterial as it is likely that the scanning would be carried out by motion of the entire head assembly or the specimen (see FIG. 4E, in which a gene chip 184 is translated in x- and y-axes). Also, for these applications it may advantageous to use a specialised system using a line of fibre bundles 186 as shown in FIG. 4F. This may have the advantage of simplicity and optical efficiency.

Other Applications including Plate Scanners and Gene Chip Readers

It may also be desirable to include systems which use a focussed line of laser light which then is scanned over the area of interest and returns through the prism as a 2D pattern containing the spectral information of all the areas of interest covered by the excitation line. This could be conveyed via the fibre bundle and projected onto a 2D CCD chip to gain the information of the image line by line.

The following points should be noted regarding this optical arrangement.
1) In most cases the area to be imaged is a flat plane and therefore does not need confocal isolation.
2) It is likely that a line scan using the prism arrangement, imaging directly onto a CCD is already known.
3) Some fast scan system point scanners may not be suitable for quantum dots and other narrow band emission marker fluorophores which have long excited state lifetimes. A slow line scan has advantages for these markers.
4) A system, which puts the CCD chip in the head itself, is likely to encounter stray excitation light. Blocking this by a long pass filter may result in filter fluorescence difficulties.
5) The long path in the Detector Unit allows a narrow band holographic blocking filter to operate and be used. This filter does not fluoresce, has a very high cut off for the excitation wavelength and also transmits fluorescence, which is very close to the excitation wavelength.

Ultra Miniaturisation

Preferred Optical Arrangement for Proximal Scan Embodiment

The principle of using a prism as a beam-splitter can be applied to a system in which the scanning is all done at the proximal end of the fibre bundle. This would eliminate the necessity of having scan mechanisms at the endoscope tip and would result in a very compact system.

This embodiment will have an optical resolving power that is reduced by a factor of 2.5 to 3 compared with the previous embodiments. This is the result of under sampling; the Nyquist resolution criterion is not fulfilled for images transferred by fibre bundle.

Figure 5:
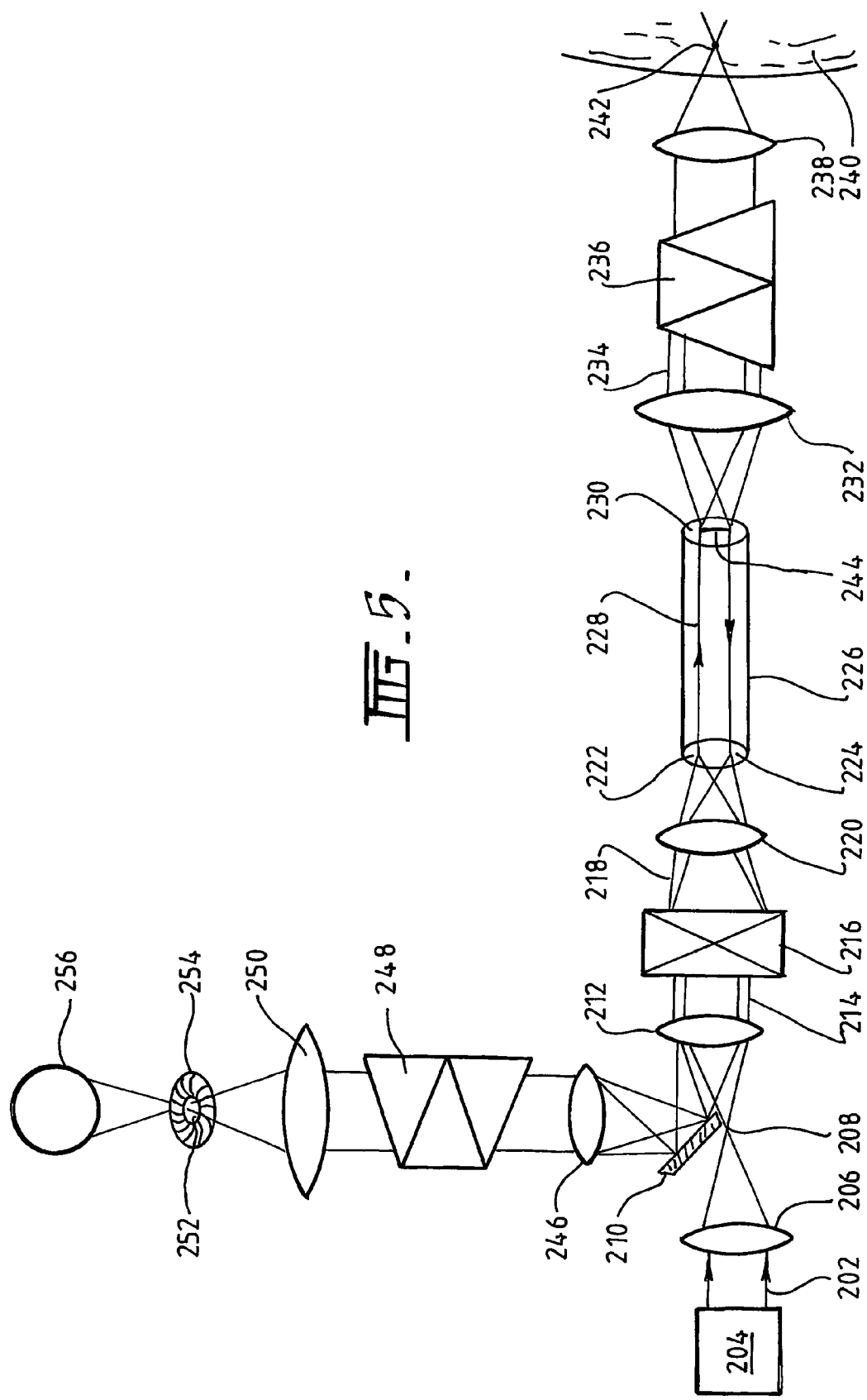
FIG. 5 is a schematic view of a laser scanning confocal microscope with fibre bundle return according to a still further embodiment of the present invention, in which scanning is performed at the proximal end of the fibre bundle.

FIG. 5 is a schematic view of a laser scanning confocal microscope system in which light 202 from a laser 204 is focussed by a lens 206 to diffraction limited spot 208 that grazes the edge of a mirror 210. The light diverges from this focus until it reaches collimating lens 212, which collimates the beam 214 and passes it through an XY scanning mechanism 216. The scanned beam 218 passes to a focussing lens 220 which focuses the beam as a spot 222 scanned as a raster or other pattern across the polished end 224 of a 'coherent' (i.e. image orientation maintaining) optical fibre bundle 226; the light then passes along fibre 228. Light emitted from fibre 228 at the other end 230 of the fibre bundle 226 diverges out to lens 232 and is converted to a collimated beam 234. This light passes through a direct vision spectroscope prism 236 and is focussed by lens 238 into a tissue sample 240 within which it forms a diffraction limited volume spot 242. Fluorescence generated at this focal volume travels back through the lens 238 to the prism 236. The fluorescence light, being of a larger wavelength is refracted less than the blue laser excitation light and it emerges as a beam which is focussed by lens 232 to a line 244 at the polished optic fibre bundle end 230 and this is transferred along the bundle and emerges at the other end 224. The light is descanned by the XY scanner 216, focussed by lens 212 to a line, intercepted by the mirror 210 and reflected through further lens 246 and second prism 248, which is reversed with respect to the initial prism 236. The second prism 248 renders the beams of all the spectral colours parallel and thus when they pass through subsequent lens 250 they are all brought to a diffraction limited focus at 252. This focus is at the centre of the pupil of a variable iris diaphragm 254 which can be adjusted to include a selected fraction of the near confocal light to pass with the fully confocal light and to impinge on the photomultiplier tube 256 and thus to produce the signal.

Figure 6:
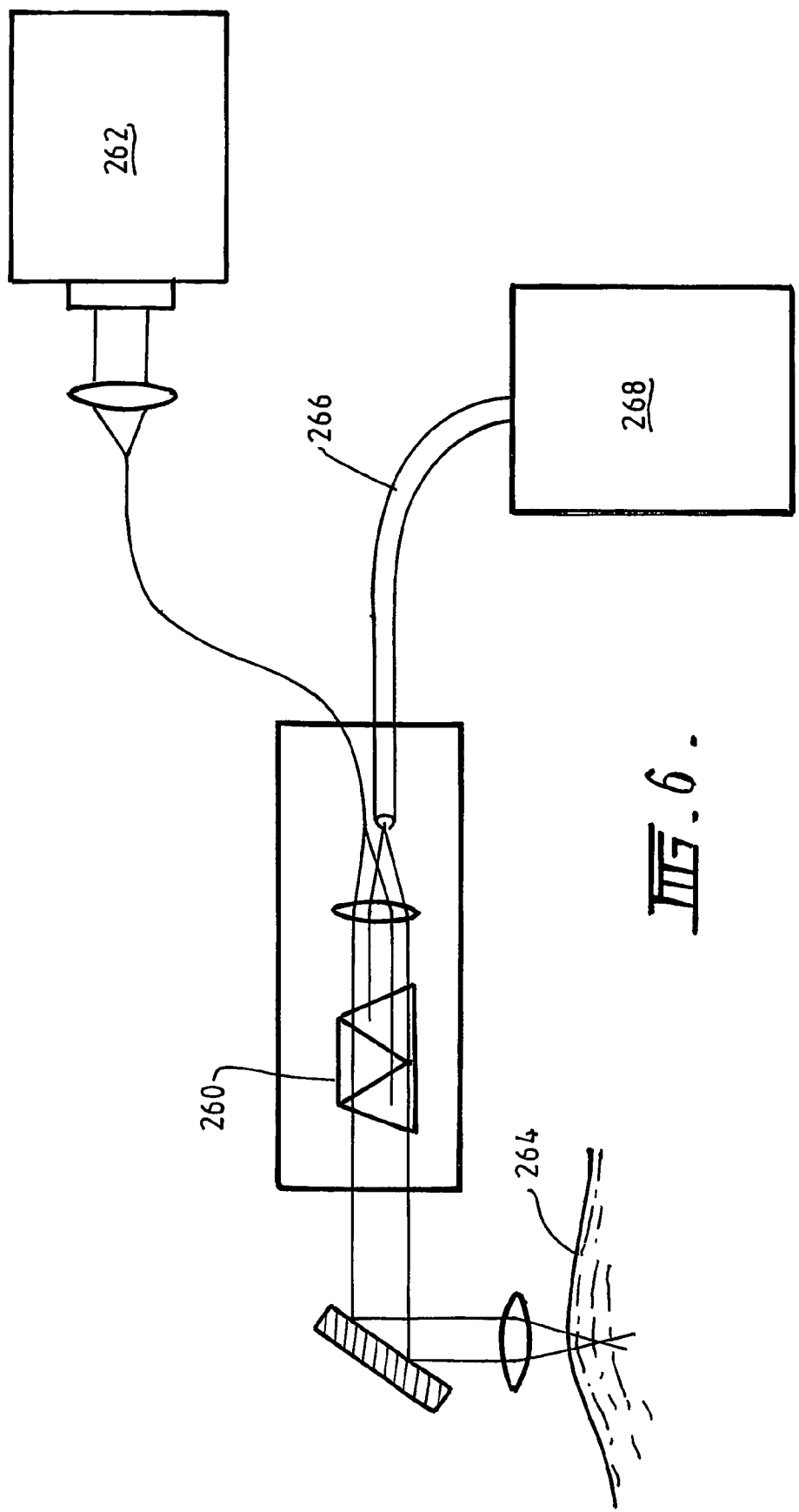
FIG. 6 is a view of a variation of the microscope of FIG. 5.

Referring to FIG. 6, the knife edge beam-splitter arrangement provided by locating mirror 210 adjacent to the beam path could be replaced by a conventional dichroic or polarisation beam-splitter 260. Also shown in this figure are laser 262, tissue sample 264, fibre bundle 266 and detector unit 268.

Mirror Scan Vibration and Damping

It might appear that, with a mirror scan at 850 Hz, unbalanced reaction forces could lead to damping problems due to transfer of vibration through the case. The mass distribution in the various embodiments, however, results in a very high moment of rotational inertia. Vibrational counter balancing should not be necessary if the fast scan mirror frame is rigidly attached to the main structural assembly. A micro machined silicon torsion mirror would be ideal from the point of view of size, but an Electro-Optical Products Corporation resonant scan mirror is also suitable.

Hybrid Systems

There are a number of variations in configuration of the preceding optical systems, which can offer some advantages.

For example, in one embodiment the slow scanning mechanism operates by the vibration of the delivery fibre and bundle. The fast scan mechanism could operate by the motion of a lens or a mirror on the other side of the prism. This configuration would eliminate one source of return "spot wander".

In another embodiment, the laser delivery fibre is scanned while the fibre bundle remains stationary. The descanning is then achieved by synchronized motion of a suitable optical component in the head. This approach may, however, involve an undesirable degree of complexity in arranging the synchronous scanner.

An alternative possibility is for the fibre bundle in the head to be moved by the slow scanning mechanism but not to be moved by the fast scan mechanism.

These designs would make it possible to use the existing tuning fork mechanism unchanged, as there is no extra mass to be scanned. The second design described above can also be used without descanning being required in the Detector Unit. This is achieved by using the slit as the confocal light isolation mechanism. These embodiments would benefit from the use of a prism combination in which the fluorescence spectrum is "bunched up" and is well separated from the excitation line. In general the slow scan mechanism is capable of moving bulky or heavy components while the fast scan mechanism cannot.

It would also be possible for the slow scan mechanism to carry the collimating lens and the prism as well as the tuning fork (with the fibre bundle) in the slow scan of the raster. This configuration would have the advantage that it would eliminate one of the sources of "spot wander".

Fibre Characteristics

Optical Transfer Efficiency, Cladding Thickness and Cross Talk between Fibres

The theoretical area fraction for identical size circles packed in a square array is 71% and for hexagonal packing 86%, but in practice the actual area fraction obtained for a bundle of fibres is generally considerably lower. It is possible that, if a plane wave is incident on a large area of fibre bundle tips and in the absence of cladding, evanescent wave involvement can produce some improvement in the proportion of light that will be guided by the bundle. Generally, however, each fibre will require cladding, however, to prevent the leakage of light from one fibre to the next at the point of contact (viz. cross talk), and the cladding will further reduce the fraction of the light transmitted by the bundle. In some applications of this type of imaging, however, cross talk may be a lesser problem than it is for conventional exidoscopy, in which case thinner cladding can be employed.

Optical Transfer Efficiency of Bundles

Measurements by Optiscan staff have put the optical transfer efficiency for fused bundles over 50%. This figure includes end reflection.

Size, N.A and Modal Characteristics of Cores of the Return Fibres in the Bundles It is desirable that the diameter of the return fibre cores be considerably less than the diameter of the excitation laser delivery fibre. This implies a corresponding increase in the numerical aperture or N.A. of the fibres. (The term N.A. for a single moded fibre is used herein to refer to the angle of the cone of light emitted from a fibre that includes a certain specified fraction of the optical energy being emitted. Unlike a multimode fibre or an imaging lens, this definition of N.A does not involve a sharp cut off of light at an edge.)

With small diameter (high numerical aperture) return fibres the confocal spectral line are spread over a width covering 3 or more lines of fibres if they are single moded. This allows the full resolving power and focal plane resolution. Most fibres in test bundles were found to have high N.A., and manufacturers quote values of 0.3 to 0.4. However, most fibre bundle cores are not single moded at visible wavelengths but, rather, support a few modes. This is probably a trade off against light loss in the cladding necessary to prevent cross talk between fibres in the bundles.

Another factor to be considered is that the optical configuration of these proposed systems however is such that the specimen (objective) lens is considerably over filled. Consequently the Airey disc of the return spot is larger than the core or modal field diameter of the laser emission fibre. This works advantageously in this parameter trade off.

As is apparent from the above discussion, the N.A. and the mode acceptance characteristics of the cores, in the bundles that have been tested, produce focal plane isolation that is not far away from that of an optimised spot scan conventional confocal system.

Fibre Bundle Stiffness

Two types of coherent (in the sense of image orientation maintaining) light guide arrays are available: 1) all glass fused fibre bundles, and 2) bundles made by winding fibre onto a rotating mandrel. The latter, wound bundles, are very flexible because the individual fibres can each bend independently like a clump of hair. Fused bundles are much stiffer. Commercially available fused imaging bundles containing 8,000-10,000 cores have been found to be too stiff to be used in the flexible tip endoscope, but such bundles with 2,000 cores have been found to transfer the spectral line to the detector unit satisfactorily and to have the required degree of flexibility. Indeed, the applicant's experience suggests that a bundle of 1,000 cores or even somewhat fewer would also transfer the spectral line to the detector unit satisfactorily.

Fibre Fluorescence

Fused bundles, being all glass, show very little fluorescence. The wound bundles however are quite fluorescent, probably due to the glues, which are used to infiltrate the region of the hank, which is to be cut and polished. An alternative source of fluorescence is the organic coating applied to the fibre as it is drawn prior to winding on the spool. This is to prevent micro scratches and brittleness of the fibre in use. If the flexible wound bundles are to be used it may be necessary to design the head to minimize stray excitation wavelength light being reflected back into the bundle. Also low fluorescence glues and coating materials may be available.

Delivery of Excitation Light by Means of Multimode Fibres (or Multimode Laser)

Delivery of the laser light by means of a multimoded fibres could be used for microplate array or gene chip readers or for other remote spectroscopy purposes. It would offer the advantage of a less intense reading spot with reduced possibility of saturation of the fluorophore. It is less likely that multimode fibre would be of advantage for imaging purposes.

It should be noted, however, that mode scrambling can be obtained by rapid movement of the fibre of illumination of the excitation spot, although the experience of the applicant suggests that it is unlikely that this would be of significant benefit.

Fibre Tip Pattern and Orientation

The natural packing pattern in the fabrication of bundles is hexagonal. Square packing bundles are very difficult to make. If the return confocal light line was of the same width as the diameter of the return fibre core (i.e. similar core characteristics for delivery and return cores), highest resolution would be obtained by positioning the bundle so that the line fell squarely along a row of fibre tips, preferably of square packed fibre. To achieve this would involve a difficult adjustment process in the head.

It may be more desirable to use return cores, the diameter of which was considerably smaller than the width of the confocal return line. This would make the orientation and packing pattern unimportant. The possibility of using a linear array of large core return fibres for the microplate readers and the like has already been mentioned.

Minimization of Stray Excitation Light

The design aim and geometry of these systems means that the emission and collection fibres are close together. Consequently some reflected laser excitation light from scattering in the head will fall on the fibre bundle and will be conveyed to the photo detector. To minimize the spurious signal from this source it would be desirable to use a narrow band laser light exclusion filter. Narrow band holographic filters are available with extinction coefficients of 6-8 orders of magnitude for a 5-10 nm band centred on the laser wavelength. For these to operate they must be located in the optical path where the beam is collimated (or within a few degrees of collimation). A suitable position is shown in the detector unit. Kaiser Optical supplies such filters.

Operation of System with Laser in the Head

Blue and near ultraviolet lasers based on Gallium Nitride have been used in confocal microscopes, but they are still connected using optic fibre delivery. Compact lasers such as laser diodes and frequency doubled YAG lasers are now sufficiently small that they could be located in the head itself.

Figure 7:
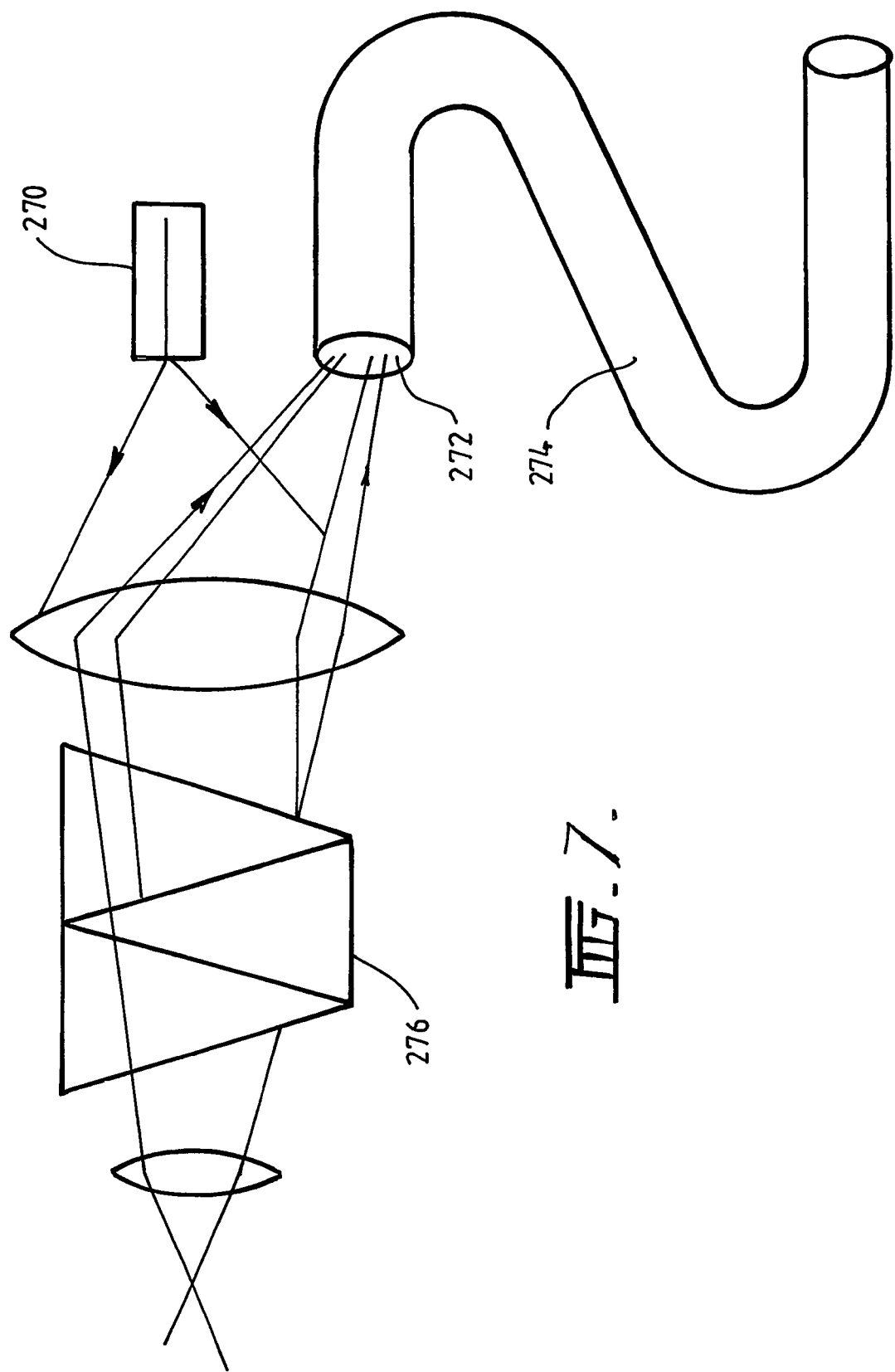
FIG. 7 is a schematic view of a laser scanning confocal microscope with fibre bundle return according to a still further embodiment of the present invention, in which a laser diode chip is mounted beside the tip of the fibre bundle.

Referring to FIG. 7, it is possible to eliminate the delivery fibre and instead to mount a laser diode chip 270 directly beside the tip 272 of the fibre bundle 274, and to utilize the prism beam-splitter 276 and fibre bundle return as described above.

Hybrid System which Maintain Telecentricity and Pinhole Confocal Isolation

Figure 8:
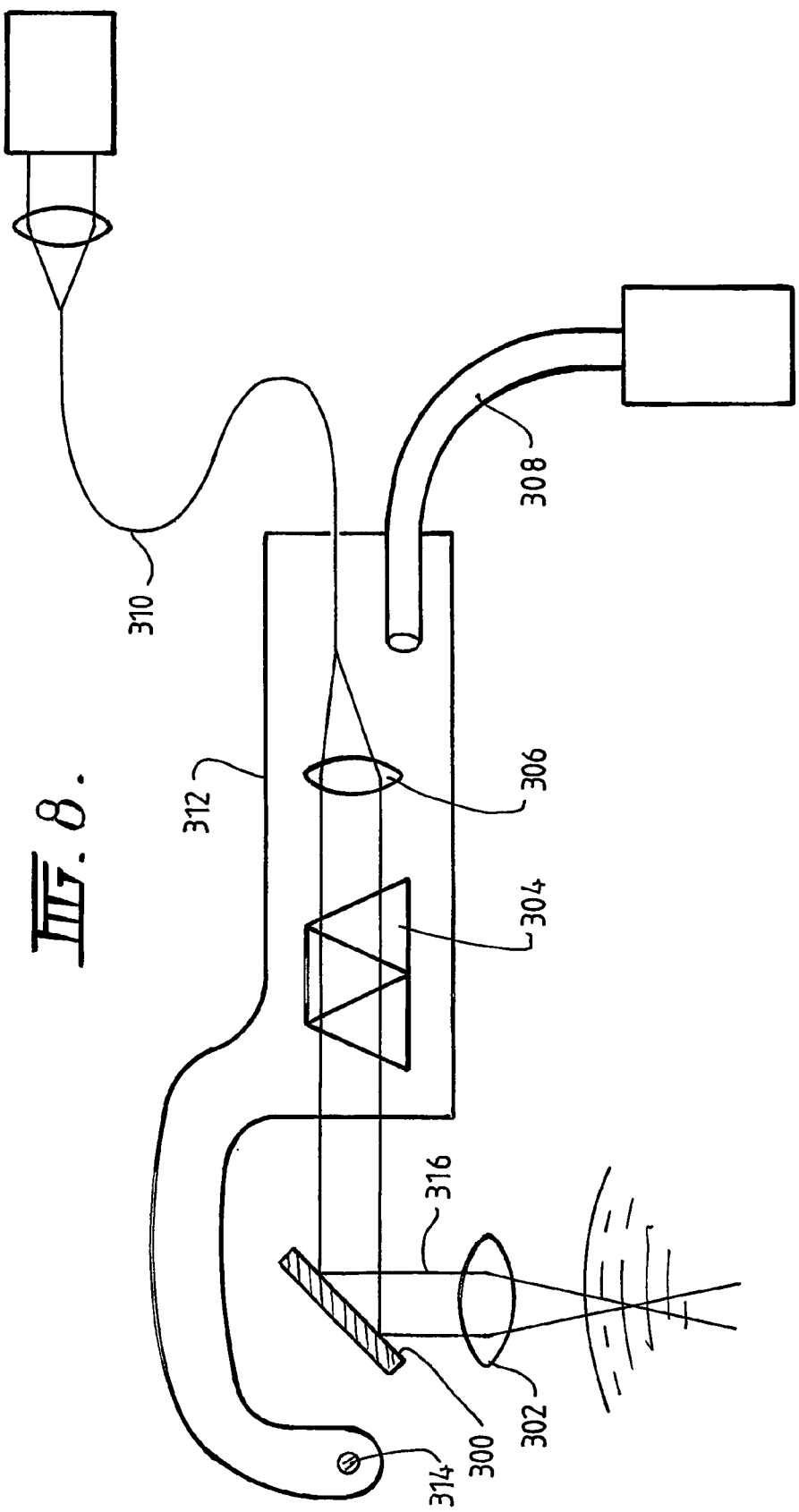
FIG. 8 is a schematic view of a scanning system for use with various embodiments of the present invention.

A compact hybrid system, which maintains scan telecentricity, is shown in FIG. 8. The fast scan resonant mirror 300 is very close to the back focal plane of objective lens 302 and thus is effectively telecentric. The prism 304, lens 306, fibre 308 and fibre bundle 310 are all rigidly mounted on a bracket 312. This bracket 312 can be rotated about a pivot 314, which means that the reflected beam 316 can be scanned about the telecentric plane of the lens.

Figure 9:
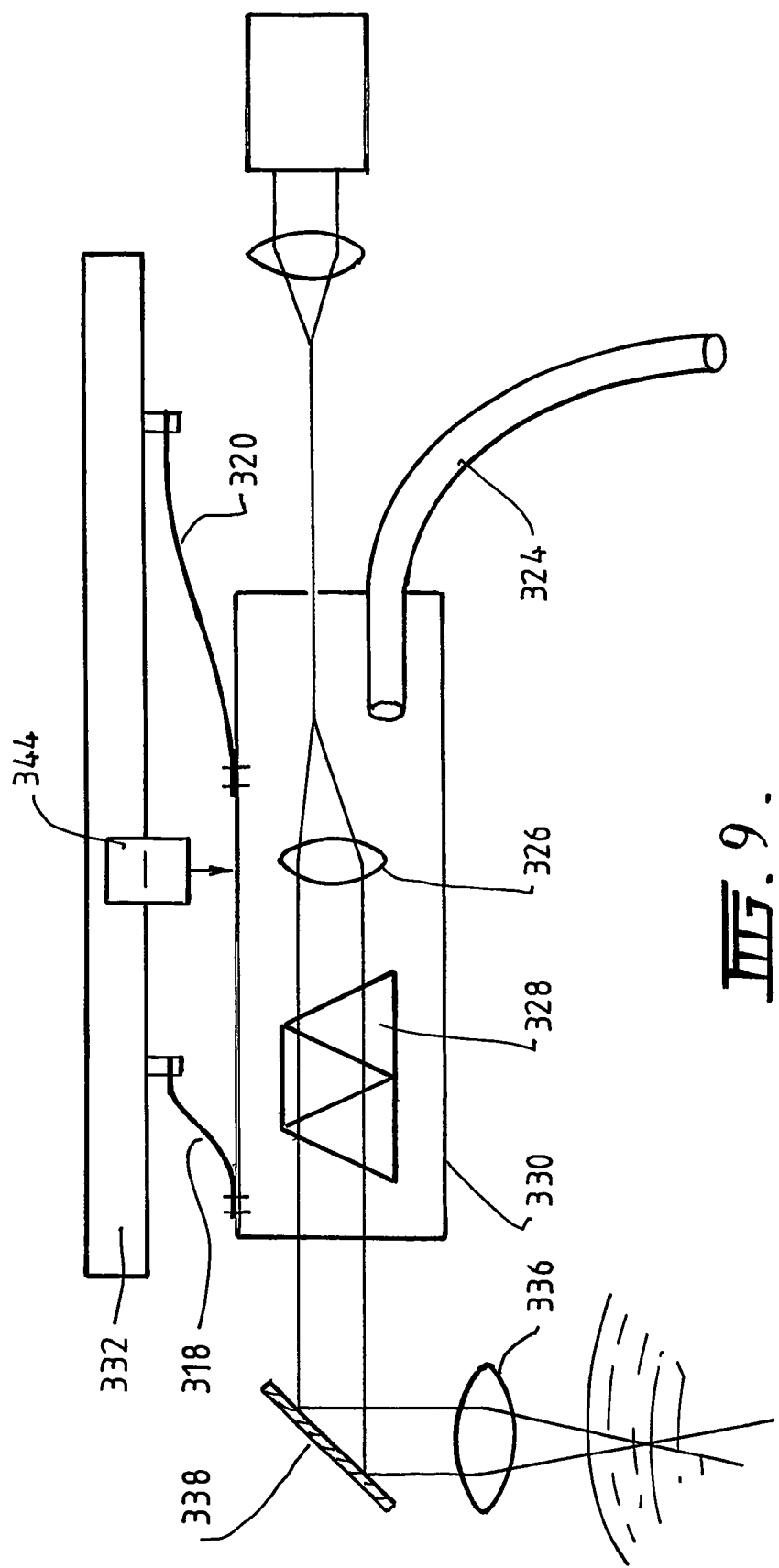
FIG. 9 is a schematic view of a further scanning system for use with various embodiments of the present invention.

A slightly more compact version uses two flexure strips 318 and 320 of unequal length is shown in FIG. 9.

In FIG. 9 the fibre 322, fibre bundle 324, collimating lens 326 and the prism 328 are held on a rigid mount 330, which is attached to the frame 332 of the endomicroscope head by two flexible strips of metal (flexure strips 318 and 320). Slow scanning motion is provided by actuator 344. The unequal lengths of the two metal strips 318 and 320 cause the mount 330 to rotate as it moves away from the frame of the endomicroscope assembly. This rotation is centred on the back focal plane of the image-producing lens 336 or, more precisely, on the reflected position of the back focal plane as imaged in a mirror 338 which is used in resonant fast scan mode.

This fast scan mirror 338 is located very close to the lens 336 and hence it is likewise operating in a close to telecentric condition.

The simultaneous operation with two or more laser lines would introduce difficulties, as the two different laser colours would each be refracted to a differing degree by the prism, and two separate spots would be focussed in the specimen. Ways of adapting hardware and software according to the present invention to deal with this would be straightforward, and within the scope of the present invention, but are likely to be of limited value.

A positive feature of the prism system, however, is that the excitation wavelength can be changed (such as from 488 nm to 514.5 nm) without the need to alter any other component (unlike dichroic beam-splitter arrangements).

Figure 10:
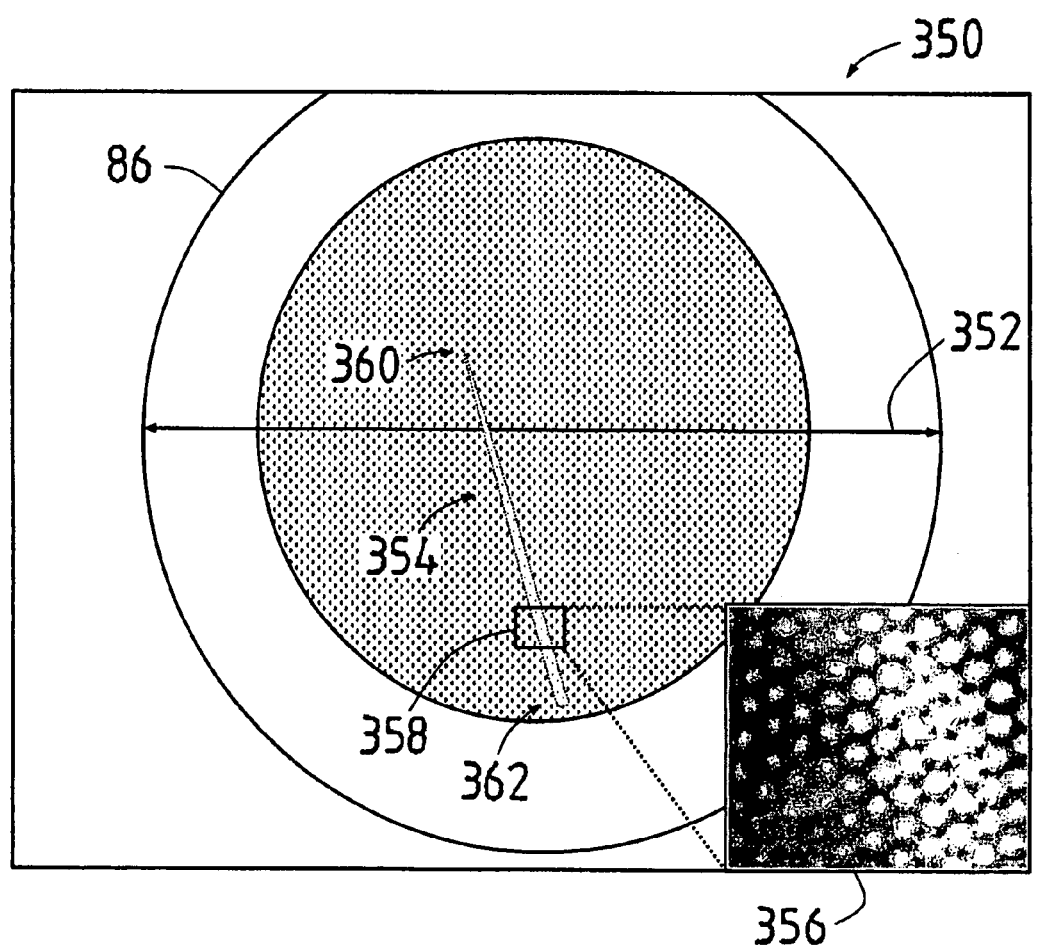
FIG. 10 is a schematic representation of a photograph of the exit end of a fibre optic bundle for use with the laser scanning confocal microscope of FIG. 2.

FIG. 10 is a schematic representation 350 of a photograph of the exit end 86 of a fibre optic bundle 82 for use with the scanning confocal microscope with fibre bundle return of FIG. 2. The photograph was taken with an Olympus (TM) brand SZ microscope; and the diameter 352 of the outer casing is 1500±100 μm and the diameter of individual fibres is 7.0±0.5 μm see insert 356 of portion 358. The illuminated line 354 (from red end 360 to green end 362) is the image of dispersed fluorescence through a direct vision prism; the insert 356 is an enlarged view of a partly illuminated portion of the individual fibre tips.

In the view of FIG. 10, the red end of the illuminated line is towards the upper left, and the blue end is towards the lower right. The boxed, enlarged portion of the illuminated line falls in the yellow region of the spectrum.

Combined Slit and Iris Diaphragm Aperture

In some optical hybrid configurations it is imaginable that an advantage might be obtained by the use of both a slit aperture and a pinhole aperture in the detector unit. The slit aperture would be positioned at the first image plane while the iris pinhole would be located in front of the photomultiplier tube.

In some embodiments, transmission or reflection diffraction gratings are used instead of prisms. The optical system could also be suitable for reflection imaging if used with polarization beam-splitter separation or an optical arrangement with a beam-splitter in the laser delivery path.

Although a number of alternatives have been mentioned above, a mirror scanning system is likely to be the most accessible scanning design for implementing the present invention, and would be readily provided in compact, handheld form.

The bundle system, when producing an image with the line fluorescence spectrum, should not introduce the image artefacts experienced with earlier two fibre systems. Any modal field mismatches should be evened out by the spread of the light over multiple fibres.

Thus, modifications within the scope of the invention may be readily effected by those skilled in the art. It is to be understood, therefore, that this invention is not limited to the particular embodiments described by way of example hereinabove.

For the purposes of this specification it should be understood that the word "comprising" means "including but not limited to", and that the word "comprises" has a corresponding meaning.

Further, any reference herein to prior art is not intended to imply that such prior art forms or formed a part of the common general knowledge.

The invention claimed is:

1. A confocal microscope or endoscope, having:
   a source of coherent light for illumination of a sample;
   a light focuser for receiving and focusing said coherent light to an illumination volume that in use intersects said sample;
   a single optical fibre for transmitting said coherent light from said source to said light focuser;
   a beam-splitter for receiving return light returned from said sample in response to said illumination and for separating from said return light a fluorescent component of said return light;
   at least one optical element for spectrally dispersing said fluorescent component; and
   an imaging optical fibre bundle of individual fibres, said fibre bundle having an entry end located to receive said dispersed fluorescent component of said return light so that said fluorescent component is transmitted to an exit end of said fibre bundle;
   wherein said dispersed fluorescent component is received and transmitted by a plurality of said individual fibres of said fibre bundle and said fibre bundle preserves, between said entry end and said exit end of said fibre bundle, the relative spatial coordinates of the cores of said individual fibres.

2. A confocal microscope or endoscope as claimed in claim 1, wherein said optical fibre comprises a single mode fibre and has an exit end mounted in a fixed spatial relationship to said entry end of said fibre bundle.

3. A confocal microscope or endoscope as claimed in claim 1, wherein said relative spatial coordinates are transformed between said ends such that an image can still be formed.

4. A confocal microscope or endoscope as claimed in claim 3, wherein said coordinates are reversed so that a mirror image is formed.

5. A confocal microscope or endoscope as claimed in claim 1, wherein said microscope or endoscope is embodied as an ophthalmoscope.

6. A confocal microscope or endoscope as claimed in claim 1, wherein said beam-splitter comprises a simple or compound prism.

7. A confocal microscope or endoscope as claimed in claim 1, wherein said beam-splitter comprises a transmission or reflection diffraction grating.

8. A confocal microscope or endoscope as claimed in claim 1, wherein said microscope or endoscope includes a further beam-splitter, optically reversed relative to said beam-splitter and located optically after said fibre bundle, to improve focal plane isolation.

9. A confocal microscope or endoscope as claimed in claim 1, wherein said microscope or endoscope includes a spatial filter optically after said fibre bundle.

10. A confocal microscope or endoscope as claimed in claim 9, wherein said spatial filter comprises a variable aperture.

11. A confocal microscope or endoscope as claimed in claim 1, wherein said microscope or endoscope includes a scanner for providing scanning of said illumination volume relative to said sample.

12. A confocal microscope or endoscope as claimed in claim 11, wherein said scanner comprises a mirror or a tuning fork.

13. A confocal microscope or endoscope as claimed in claim 11, wherein said scanner comprises a pivotably mounted member provided with collimating optics for collimating said coherent light.

14. A confocal microscope or endoscope as claimed in claim 13, wherein said collimating optics comprise a simple or compound lens.

15. A confocal microscope or endoscope as claimed in claim 13, wherein said pivotably mounted member is mounted by means of, and is pivotable about, an axle.

16. A confocal microscope or endoscope as claimed in claim 13, wherein said pivotably mounted member is mounted by means of a pair of flexible supports that differ so that said pivotably mounted member can be pivoted by being oscillated.

17. A confocal microscope or endoscope as claimed in claim 16, wherein said flexible supports differ in length.

18. A confocal microscope or endoscope as claimed in claim 1, including one or more shallow angle prisms located in an image plane to separate out different spectral bands, and a plurality of fibre bundles, each for receiving a respective spectral band, for producing multiple color images.

19. A confocal microscope or endoscope as claimed in claim 18, including a plurality of separate photo-detectors, each for detecting a respective spectral band transmitted by a respective one of said fibre bundles.

20. A confocal microscope or endoscope as claimed in claim 1, wherein said optical element for spectrally dispersing said fluorescent component comprises said beam-splitter.

21. A method of performing confocal microscopy or endoscopy, comprising:
   transmitting coherent light from a light source to a light focuser with a single optical fibre;
   focusing said coherent light with said light focuser to an illumination volume that in use intersects a sample;
   receiving return light returned from said sample in response to said illumination at a beam-splitter;
   separating a fluorescent component of said return light from said return light with said beam-splitter;
   dispersing said fluorescent component such that said fluorescent component is received by a plurality of individual fibers of an imaging optical fibre bundle at an entry end of said fibre bundle;
   transmitting said fluorescent component with said fibre bundle to an exit end of said fibre bundle; and
   preserving the relative spatial coordinates of the cores of said individual fibres between said entry end and said exit end of said fibre bundle.

* * * * *